(12) United States Patent
Tajiri et al.

(10) Patent No.: US 10,561,628 B2
(45) Date of Patent: *Feb. 18, 2020

(54) SOLID PREPARATION INCLUDING ANTIOXIDANT

(71) Applicant: DAIICHI SANKYO COMPANY, LIMITED, Tokyo (JP)

(72) Inventors: Shinichiro Tajiri, Kanagawa (JP); Jin Hisazumi, Kanagawa (JP); Shinji Yoshinaga, Kanagawa (JP); Hiroyuki Fujimori, Kanagawa (JP); Hiroaki Arai, Kanagawa (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/559,573

(22) PCT Filed: Mar. 17, 2016

(86) PCT No.: PCT/JP2016/058607
§ 371 (c)(1),
(2) Date: Sep. 19, 2017

(87) PCT Pub. No.: WO2016/148263
PCT Pub. Date: Sep. 22, 2016

(65) Prior Publication Data
US 2018/0042878 A1   Feb. 15, 2018

(30) Foreign Application Priority Data
Mar. 19, 2015   (JP) .................. 2015-055768

(51) Int. Cl.
*A61K 31/195*   (2006.01)
*A61K 9/20*   (2006.01)
*A61K 9/28*   (2006.01)

(52) U.S. Cl.
CPC .......... *A61K 31/195* (2013.01); *A61K 9/2013* (2013.01); *A61K 9/2018* (2013.01); *A61K 9/2054* (2013.01); *A61K 9/2095* (2013.01); *A61K 9/28* (2013.01)

(58) Field of Classification Search
CPC .. A61K 9/2013; A61K 9/2054; A61K 9/2095; A61K 9/28; A61K 9/20; A61K 9/2018; A61K 31/195; A61K 47/10; A61K 47/12; A61K 47/14; A61K 47/22; A61K 47/24; A61K 47/26; A61K 47/36; A61K 47/38; A61K 47/40
See application file for complete search history.

(56) References Cited

U.S. PATENT DOCUMENTS

| | | | |
|---|---|---|---|
| 5,032,390 A | 7/1991 | Iwaya et al. | |
| 6,054,482 A | 4/2000 | Augert et al. | |
| 7,351,429 B1 | 4/2008 | Ohyama et al. | |
| 7,947,738 B2 | 5/2011 | Shimada et al. | |
| 8,895,141 B2 | 11/2014 | Satomi et al. | |
| 9,675,570 B2 | 6/2017 | Tajiri et al. | |
| 2001/0004637 A1* | 6/2001 | Hanamura ........... | A61K 9/0014 514/282 |
| 2005/0026981 A1 | 2/2005 | Sugihara et al. | |
| 2007/0099986 A1 | 5/2007 | Ishichi et al. | |
| 2009/0041843 A1 | 2/2009 | Kozaki et al. | |
| 2010/0062063 A1 | 3/2010 | Umejima et al. | |
| 2010/0249229 A1* | 9/2010 | Shimada ............... | C07C 229/32 514/530 |
| 2011/0135927 A1 | 6/2011 | Satomi et al. | |
| 2011/0305758 A1 | 12/2011 | Matono et al. | |
| 2012/0071685 A1 | 3/2012 | Kitagawa et al. | |
| 2012/0156261 A1 | 6/2012 | Fujiwara et al. | |
| 2012/0219637 A1* | 8/2012 | Aniket ................. | A61K 9/0056 424/617 |
| 2012/0294947 A1 | 11/2012 | Kuninobu et al. | |
| 2012/0294957 A1 | 11/2012 | Kuninobu et al. | |
| 2013/0243859 A1* | 9/2013 | Mima ................. | A61K 31/4439 424/465 |
| 2013/0309313 A1* | 11/2013 | Gareau .................... | A23L 7/126 424/492 |
| 2013/0345444 A1* | 12/2013 | Yamano ................. | C07F 15/006 556/21 |
| 2014/0024699 A1* | 1/2014 | Kaelin, Jr. .......... | C12N 15/1137 514/44 A |
| 2014/0030209 A1* | 1/2014 | Furuta .................. | A61K 31/415 424/78.07 |
| 2015/0079166 A1* | 3/2015 | Tajiri ..................... | A61K 47/10 424/464 |

FOREIGN PATENT DOCUMENTS

CN   101878193 A1   11/2010
EP    1 205 190 A1   5/2002
(Continued)

OTHER PUBLICATIONS

Tajiri et al .Machine Translated WO 2014163132 A1 2014.*
(Continued)

*Primary Examiner* — Blessing M Fubara
(74) *Attorney, Agent, or Firm* — Dorsey & Whitney LLP

(57) ABSTRACT

An object of the present invention is to provide [(1R,5S,6S)-6-(aminomethyl)-3-ethylbicyclo[3.2.0]hept-3-en-6-yl] acetic acid monobenzenesulfonate as a stabilized pharmaceutical solid preparation, and also to provide a method for preparing the stabilized pharmaceutical solid preparation. The object can be attained by a pharmaceutical solid preparation comprising [(1R,5S,6S)-6-(aminomethyl)-3-ethylbicyclo[3.2.0]hept-3-en-6-yl]acetic acid monobenzenesulfonate which is a compound represented by the following formula (I) in combination with (i) one or two or more excipients, (ii) one or two or more disintegrants, and (iii) a specific antioxidant.

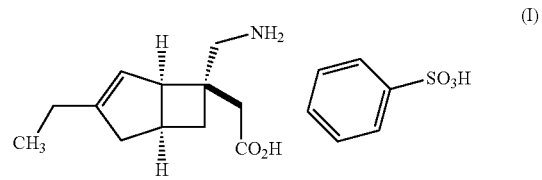

(I)

16 Claims, No Drawings

(56) References Cited

FOREIGN PATENT DOCUMENTS

| | | |
|---|---|---|
| EP | 2826477 A1 | 1/2015 |
| EP | 3 272 346 A1 | 1/2018 |
| JP | 11-189547 A | 7/1999 |
| JP | 2001-064177 A1 | 3/2001 |
| JP | 2003-104887 A | 4/2003 |
| JP | 2005-263790 A | 9/2005 |
| JP | 2007-131542 A | 5/2007 |
| JP | 2009-275041 A | 11/2009 |
| JP | 4479974 B2 | 6/2010 |
| JP | 2010-241796 A | 10/2010 |
| JP | 2013-35797 A | 2/2013 |
| WO | WO 01/12193 A1 | 2/2001 |
| WO | WO 2001/034147 A1 | 5/2001 |
| WO | WO 2006/056874 A1 | 6/2006 |
| WO | WO 2007/052592 A1 | 5/2007 |
| WO | WO 2010/021300 A1 | 2/2010 |
| WO | WO 2010/087462 A1 | 8/2010 |
| WO | WO 2013/021660 A1 | 2/2013 |
| WO | WO 2014/163132 A1 | 10/2014 |

OTHER PUBLICATIONS

Cutrignelli et al., "Comparative effects of some hydrophilic excipients on the rate of gabapentin and baclofen lactamization in lyophilized formulations," *International Journal of Pharmaceutics*, (2007), 332:98-106.

Hashida, "The Design and Evaluation of Oral Medications," Published Feb. 10, 1995, by Yakugyo Jiho Co., Tokyo, Japan, pp. 50-51.

Tsuda et al., "Pharmaceutical Engineering, Course X, Fundamentals of Pharmaceutical Development," Published Mar. 1, 1971, by Chijin Shoka Co., Ltd., Tokyo, Japan, pp. 161-162, 167, 170-171, and 179.

Yakuji Nippo Limited, Iyakuhin Tenkabutsu Jiten 2007 (English translation is "Pharmaceutical Excipients Dictionary," 2007), International Pharmaceutical Excipients Council Japan, with English translation, 50 pages.

English Translation of International Search Report dated Jun. 7, 2016, for PCT Application No. PCT/JP2016/058608, 3 pages.

English Translation of Written Opinion dated Jun. 7, 2016, for PCT Application No. PCT/JP2016/058608, 7 pages.

English Translation of International Search Report dated Jun. 7, 2016, for PCT Application No. PCT/JP2016/058607, 3 pages.

English Translation of Written Opinion dated Jun. 7, 2016, for PCT Application No. PCT/JP2016/058607, 6 pages.

English translation of International Search Report dated Apr. 28, 2014, in PCT Application No. PCT/JP2014/059812, 2 pages.

Supplementary Search Report dated Aug. 12, 2015, in European Application No. 14779687.4, 4 pages.

U.S. Appl. No. 15/559,700, filed Sep. 19, 2017, entitled "Solid Preparation Including Colorant," 28 pages.

Ferin et al., "Biological Effects and Toxicity Assessment of Titanium Dioxides: Anastase and Rutile," *American Industrial Hygiene Association Journal*, (1985), 46(2):69-72, and abstract published online at https://www.tandfonline.com/doi/pdf/10.1080/15298668591394419?needAccess=true.

* cited by examiner

SOLID PREPARATION INCLUDING ANTIOXIDANT

This application is a national stage application under 35 U.S.C. § 371 of International Application No. PCT/JP2016/058607, filed Mar. 17, 2016, entitled "SOLID PREPARATION CONTAINING ANTIOXIDANT AGENT," which claims priority to Japanese Patent Application No. 2015-055768, filed Mar. 19, 2015.

TECHNICAL FIELD

The present invention relates to pharmaceutical solid preparations of [(1R,5S,6S)-6-(aminomethyl)-3-ethylbicyclo[3.2.0]hept-3-en-6-yl]acetic acid monobenzenesulfonate (hereinafter, also referred to as "compound (I)") stabilized by containing a specific antioxidant, and methods for preparing the stabilized pharmaceutical solid preparations.

The present invention also relates to tablets of compound (I) stabilized by containing a specific antioxidant, and methods for producing the stabilized tablets.

BACKGROUND ART

Compound (I) represented by the following structural formula:

[Formula 1]

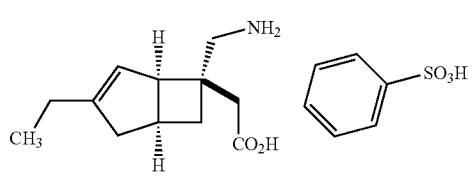

is disclosed in US 2010/249229. This compound (I) has excellent activity as an $\alpha_2\delta$ ligand and as such, is expected to have excellent therapeutic and/or preventive effects on disorders such as pain and central nervous system involvement. Also, pharmaceutical compositions containing compound (I) are disclosed in EP2826477.

CITATION LIST

Patent Literature

Patent Literature 1: US 2010/249229
Patent Literature 2: EP2826477

SUMMARY OF INVENTION

Technical Problem

The present inventors have continuously conducted diligent studies in order to develop pharmaceutical solid preparations of compound (I) stabilized by containing a specific antioxidant, and methods for preparing the stabilized pharmaceutical solid preparations. Consequently, the present inventors have solved problems associated therewith and completed the present invention.

Solution to Problem

Specifically, the present invention is based on the finding that, as described below, compound (I) represented by the following structural formula:

[Formula 2]

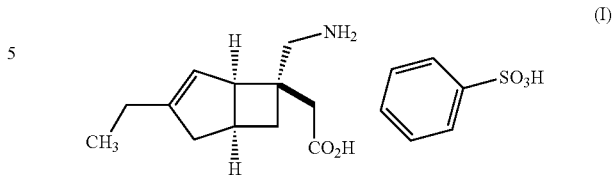

is stabilized by allowing a specific antioxidant to be present together. Thus, the present invention provides pharmaceutical solid preparations containing this compound (I) and the specific antioxidant, and methods for preparing the stabilized pharmaceutical solid preparations.

Preferred aspects of the present invention are as shown below.

[1] A pharmaceutical solid preparation comprising [(1R,5S,6S)-6-(aminomethyl)-3-ethylbicyclo[3.2.0]hept-3-en-6-yl]acetic acid monobenzenesulfonate which is a compound represented by the following formula (I):

[Formula 3]

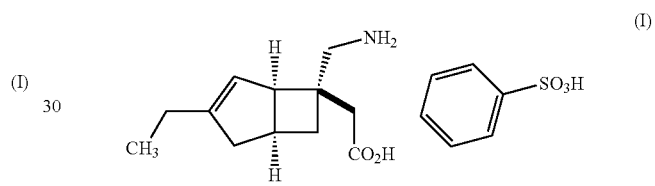

in combination with
(i) one or two or more excipients,
(ii) one or two or more disintegrants, and
(iii) a specific antioxidant.

[2] A pharmaceutical solid preparation comprising [(1R,5S,6S)-6-(aminomethyl)-3-ethylbicyclo[3.2.0]hept-3-en-6-yl]acetic acid monobenzenesulfonate which is a compound represented by the following formula (I):

[Formula 4]

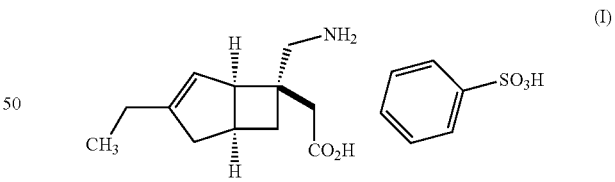

in combination with
(i) one or two or more selected from the group consisting of D-mannitol, lactose, corn starch, and crystalline cellulose,
(ii) carmellose calcium, and
(iii) a specific antioxidant.

[3] The pharmaceutical solid preparation according to [1] or [2], wherein the component (i) is D-mannitol.

[4] The pharmaceutical solid preparation according to [3], wherein the D-mannitol is D-mannitol having an average particle size of 100 μm or smaller.

[5] The pharmaceutical solid preparation according to any one of [1] to [4], wherein the specific antioxidant (iii) is any one or two or more antioxidants selected from the group consisting of sodium edetate, citric acid hydrate, dibutylhydroxytoluene, propyl gallate, magnesium citrate (anhydrous), soybean lecithin, tocopherol, tocopherol acetic acid ester, and β-cyclodextrin.

[6] The pharmaceutical solid preparation according to any one of [1] to [4], wherein the specific antioxidant (iii) is citric acid hydrate.

[7] The pharmaceutical solid preparation according to any one of [1] to [4], wherein the pharmaceutical solid preparation is a tablet, wherein the specific antioxidant (iii) is citric acid hydrate, and the amount of the citric acid hydrate used is 0.01 to 10% by weight with respect to the total weight of the uncoated tablet.

[8] The pharmaceutical solid preparation according to any one of [1] to [4], wherein the pharmaceutical solid preparation is a tablet, wherein the specific antioxidant (iii) is citric acid hydrate, and the amount of the citric acid hydrate used is 0.1 to 3.0% by weight with respect to the total weight of the uncoated tablet.

[9] The pharmaceutical solid preparation according to any one selected from [1] to [8], further comprising magnesium stearate.

[10] The pharmaceutical solid preparation according to any one selected from [1] to [9], wherein the content of the compound represented by the formula (I) (in terms of its free form) is 0.5 to 5% by weight with respect to the total weight.

[11] The pharmaceutical solid preparation according to any one selected from [2] to [10], wherein the content of the carmellose calcium (ii) is 5 to 15% by weight with respect to the total weight.

[12] The pharmaceutical solid preparation according to [9], wherein the content of the magnesium stearate is 1 to 3% by weight with respect to the total weight.

[13] A method for producing a pharmaceutical solid preparation according to any one selected from [9] to [12], comprising mixing [(1R,5S,6S)-6-(aminomethyl)-3-ethylbicyclo[3.2.0]hept-3-en-6-yl]acetic acid monobenzenesulfonate which is a compound represented by the following formula (I):

[Formula 5]

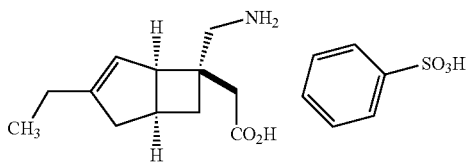

with
(i) one or two or more selected from the group consisting of D-mannitol, lactose, corn starch, and crystalline cellulose,
(ii) carmellose calcium, and
(iii) a specific antioxidant
and subsequently with magnesium stearate by addition, followed by a direct compression method to produce a tablet.

[14] A method for stabilizing a pharmaceutical solid preparation in the case of producing the pharmaceutical solid preparation using [(1R,5S,6S)-6-(aminomethyl)-3-ethylbicyclo[3.2.0]hept-3-en-6-yl]acetic acid monobenzenesulfonate which is a compound represented by the following formula (I):

[Formula 6]

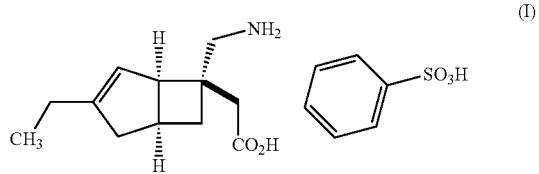

in combination with
(i) one or two or more selected from the group consisting of D-mannitol, lactose, corn starch, and crystalline cellulose,
(ii) carmellose calcium, and
(iii) a specific antioxidant,
the method comprising stabilizing the produced pharmaceutical solid preparation using the specific antioxidant.

Advantageous Effects of Invention

The present invention has overcome various difficulties in obtaining a stabilized pharmaceutical solid preparation of compound (I). A feature of the present invention is that the stabilized pharmaceutical solid preparation can be obtained at last by containing a specific antioxidant.

The present invention has enabled the preparation of a stabilized pharmaceutical solid preparation of compound (I).

DESCRIPTION OF EMBODIMENTS (Components and their Preferred Contents)

The compound (I) used as an active ingredient in the present invention has individual particle sizes of preferably 60 μm (more preferably 40 μm) or smaller in terms of d50 particle size.

The content of compound (I) (in terms of its free form) used in the present invention is preferably 0.5 to 40% by weight, more preferably 0.5 to 25% by weight, particularly preferably 0.5 to 10% by weight (more particularly preferably 0.5 to 5% by weight), with respect to the total weight.

In the present invention, excipient refers to a component that is described in general references regarding preparations and is added for the purpose of adjusting sizes or concentrations to given ones in the formulation of tablets, etc.

The content of excipient (preferably D-mannitol) used in the present invention is preferably 50 to 90% by weight, more preferably 60 to 90% by weight with respect to the total weight.

The average particle size of the D-mannitol used in the present invention is desirably smaller than 150 μm, preferably 120 μm or smaller, more preferably 100 μm or smaller, particularly preferably 80 μm or smaller.

In the present invention, disintegrant refers to a component that is described in general references regarding preparations and is added for the purpose of facilitating releasing an active ingredient by, for example, absorbing water in the body for swelling and thereby disintegrating tablets.

The content of disintegrant (preferably carmellose calcium, etc.) used in the present invention is preferably 2 to 20% by weight, more preferably 5 to 15% by weight, with respect to the total weight.

The content of binder (preferably hypromellose, etc.) used in the present invention is preferably 5 to 20% by weight with respect to the total weight.

The content of lubricant (preferably magnesium stearate, sodium stearyl fumarate, etc., particularly preferably magnesium stearate) used in the present invention is preferably 0.5 to 5% by weight, more preferably 1 to 3% by weight, with respect to the total weight.

The specific an antioxidant used in the present invention is antioxidant whose use is generally acceptable in the medical field. Examples thereof include citric acid hydrate, sodium edetate, sodium bisulfite, dibutylhydroxytoluene, tocopherol, sodium sulfite, ascorbic acid, 1,3-butylene glycol, sodium pyrosulfite, butylhydroxyanisole, tocopherol acetic acid ester, dried sodium sulfite, soybean lecithin, propyl gallate, magnesium citrate (anhydrous), erythorbic acid, sodium thioglycolate, ascorbyl palmitate, alpha-thioglycerin, sodium nitrite, L-ascorbyl stearate, cysteine hydrochloride, benzotriazole, sodium thiomalate, natural vitamin E, potassium dichloroisocyanurate, d-δ-tocopherol, mixed tocopherol concentrates, pentaerythrityl-tetrakis[3-(3,5-di-t-butyl-4-hydroxyphenyl)propionate], 2-mercaptobenzimidazole, magnesium citrate, and β-cyclodextrin.

Sodium edetate, citric acid hydrate, dibutylhydroxytoluene, propyl gallate, magnesium citrate (anhydrous), soybean lecithin, tocopherol, tocopherol acetic acid ester, β-cyclodextrin, or the like is preferred.

The amount of the antioxidant used differs in optimum amount depending on the type of the antioxidant. When the antioxidant is, for example, citric acid hydrate, its weight is preferably 0.01 to 10% by weight, more preferably 0.02 to 10% by weight, further preferably 0.1 to 5.0% by weight, with respect to the total weight.

In the tablet according to the present invention, the preferred content of each component with respect to the total weight of its uncoated tablet is as follows:

Compound (I) (in terms of its free form): 0.5 to 25% by weight

Excipient (preferably D-mannitol): 50 to 90% by weight (average particle size: smaller than 150 μm)

Disintegrant (preferably carmellose calcium): 2 to 20% by weight

Lubricant (preferably magnesium stearate): 0.5 to 5% by weight

The content of each component is more preferably as follows:

Compound (I) (in terms of its free form): 0.5 to 10% by weight

Excipient (D-mannitol): 60 to 90% by weight (average particle size: 100 μm or smaller)

Disintegrant (carmellose calcium): 5 to 15% by weight

Lubricant (magnesium stearate): 1 to 3% by weight

Antioxidant: 0.02 to 10% by weight, for example, 3% by weight of citric acid hydrate is used.

(Method for Producing Solid Preparation)

The solid preparation of the present invention is obtained in the form of tablets, coated tablets, or the like by sequentially subjecting a powder of compound (I) serving as an active ingredient to, for example:

(1) a step of adding stabilizers such as an excipient and a disintegrant, and further adding auxiliaries necessary for formulation (a lubricant, etc.);

(2) a tableting step of compressing the resulting granular powder using a tableting machine; and (3) an optional coating step of coating the surface of the resulting tablets.

Examples of the method for producing the solid preparation include:

(1) a direct compression method which involves mixing the active ingredient with additives and directly compression-molding the mixture using a tableting machine;

(2) a semi-direct compression method which involves granulating additives, mixing the granules with the active ingredient, and compression-molding the mixture;

(3) a dry granule compression method which involves granulating the active ingredient and additives by a dry process, then adding a lubricant, etc. to the granules, and compression-molding the mixture; and (4) a wet granule compression method which involves granulating the active ingredient and additives by a wet process, then adding a lubricant, etc. to the granules, and compression-molding the mixture.

An approach such as fluidized-bed granulation, high-speed mixer granulation, or melt granulation can be used as a granulation method.

In the present invention, a method which involves preparing a tablet by directly compressing a mixed powder of the active ingredient without granulating a powder of the active ingredient is preferred.

For example, the method for producing a tablet according to the present invention is performed as described below.

The compound (I) serving as an active ingredient is pulverized. The particle size of the resulting powder is adjusted. Then, an excipient and/or a disintegrant are added to the powder, followed by mixing. Then, the mixture is sifted through a particle size selector. Then, a lubricant is added thereto, followed by further mixing. Then, the mixture is compressed using a tableting machine to obtain uncoated tablets.

The obtained uncoated tablets are prepared into film-coated tablets using a coating apparatus.

Hereinafter, the present invention will be described in more detail with reference to the Examples. However, it should be understood that the Examples below are provided merely for describing the present invention and are not intended to limit the present invention.

EXAMPLES (Example 1) Stability of Dibutylhydroxytoluene and Preparation (1) Preparation of Example 1

Dibutylhydroxytoluene was pulverized at the number of revolutions of 18000 rpm using a centrifugal pulverizer (ZM-100, Nippon Seiki Co., Ltd.). Compound (I), D-mannitol, carmellose calcium, and the dibutylhydroxytoluene were weighed at mixing ratios shown in Table 1 and mixed for 5 minutes at the number of revolutions of 39 rpm using a V-shaped mixer (2 L).

The mixture was sifted at 600 rpm using COMIL (QC-U-5, Φ1.143, QUADRO) to prepare a sifted powder.

Subsequently, magnesium stearate was weighed at a mixing ratio shown in Table 1 and added to the sifted powder, followed by mixing for 3 minutes at the number of revolutions of 32 rpm using a V-shaped mixer (2 L).

The mixture was molded at a compressive pressure of approximately 7.5 kN using a tableting machine (Virgo, Kikusui Seisakusho Ltd.) to obtain uncoated tablets (active ingredient (in terms of free form): 2.5%, oblong tablets, 8.4×4.4 mm) each having a tablet mass of 100 mg.

The tablets were film-coated using a coating apparatus (High Coater Labo 30, Freund Corp.) at a charge air temperature of 65° C., a spray rate of approximately 7.5 g/min, and an exhaust gas temperature of approximately 34° C. (endpoint).

(2) Preparation of Comparative Example 1

Compound (I), D-mannitol, and carmellose calcium were weighed at mixing ratios shown in Table 1 and mixed for 5 minutes at the number of revolutions of 39 rpm using a V-shaped mixer (2 L).

The mixture was sifted at 600 rpm using COMIL (QC-U-5, Φ1.143, QUADRO) to prepare a sifted powder.

Subsequently, magnesium stearate was weighed at a mixing ratio shown in Table 1 and added to the sifted powder, followed by mixing for 3 minutes at the number of revolutions of 32 rpm using a V-shaped mixer (2 L).

The mixture was molded at a compressive pressure of approximately 7.5 kN using a tableting machine (Virgo, Kikusui Seisakusho Ltd.) to obtain uncoated tablets (active ingredient (in terms of free form): 2.5%, oblong tablets, 8.4×4.4 mm) each having a tablet mass of 100 mg.

The tablets were film-coated using a coating apparatus (High Coater Labo 30, Freund Corp.) at a charge air temperature of 65° C., a spray rate of approximately 7.5 g/min, and an exhaust gas temperature of approximately 34° C. (endpoint).

TABLE 1

| | Composition (mg/tablet) | |
|---|---|---|
| Component contained | Example 1 | Comparative Example 1 |
| Compound (I) | 4.39 | 4.39 |
| (mg in terms of free form) | (2.5) | (2.5) |
| D-mannitol | 83.51 | 83.61 |
| (Parteck M100, Merck) | | |
| Carmellose calcium | 10 | 10 |
| (E.C.G-505, Gotoku Chemical Co., Ltd.) | | |
| Dibutylhydroxytoluene | 0.1 | — |
| (Wako Pure Chemical Industries, Ltd.) | | |
| Magnesium stearate | 2 | 2 |
| (Parteck LUB, Merck) | | |
| OPADRY ® OY-S-9607 | 4.88 | 4.88 |
| (Colorcon Japan LLC) | | |
| (Hypromellose) | 3.6 | 3.6 |
| (Titanium oxide) | 0.58 | 0.58 |
| (Talc) | 0.7 | 0.7 |
| Red iron sesquioxide | 0.04 | 0.04 |
| (Rockwood Holdings, Inc.) | | |
| Yellow iron sesquioxide | 0.08 | 0.08 |
| (Rockwood Holdings, Inc.) | | |
| Total | 105 | 105 |

(3) Evaluation Method and Results

The tablets of Example 1 and Comparative Example 1 were left under conditions involving 25° C., 75% RH, and 1 month or 25° C., 75% RH, and 3 months. Then, the amount of related substances was measured by HPLC (1290 Infinity, Agilent Technologies, Inc.).

The results are shown in Table 2. The amount of increase from the initial total amount of related substances was shown to be 1/20 or less in the tablets containing dibutylhydroxytoluene, as compared with the tablets free from dibutylhydroxytoluene.

TABLE 2

| Condition | Example 1 | Comparative Example 1 |
|---|---|---|
| 25° C./75% RH/1 month Open condition | 0.10% | 3.74% |

TABLE 2-continued

| Condition | Example 1 | Comparative Example 1 |
|---|---|---|
| 25° C./75% RH/3 months Open condition | 0.34% | 7.06% |

(Examples 2 to 10) Formulation Stability of Additive and Preparation (1) Preparation of Example 2

Sodium edetate was pulverized at the number of revolutions of 1800 rpm using a beta mill (RM-201, manufactured by Medicatec Inc.). Compound (I), D-mannitol, carmellose calcium, and the sodium edetate were weighed at mixing ratios shown in Table 3 and mixed for 5 minutes in a 13K bottle.

The mixture was sifted through a 1000-μm mesh sieve and then sifted through a 300-mesh sieve to prepare a sifted powder.

Subsequently, magnesium stearate was weighed at a mixing ratio shown in Table 3 and added to the sifted powder, followed by mixing for 5 minutes in a 13K bottle.

The mixture was molded at a compressive pressure of approximately 10 kN using a tableting machine (HandTab-200, Ichihashi Seiki Co., Ltd.) to obtain uncoated tablets (active ingredient (in terms of free form): 2.5%, round tablets, ⌀10.5 mm) each having a tablet mass of 400 mg.

(2 to 5) Preparation of Examples 3 to 6

Uncoated tablets supplemented with citric acid hydrate, dibutylhydroxytoluene, gallic acid ester, and magnesium citrate (anhydrous) were produced according to the preparation procedures of Example 2.

(6) Preparation of Example 7

Compound (I) and D-mannitol were weighed at mixing ratios shown in Table 3 and added to soybean lecithin and carmellose calcium mixed in advance at mixing ratios shown in Table 3 using a mortar, followed by mixing for 5 minutes in a 13K bottle.

The mixture was sifted through a 1000-μm mesh sieve and then sifted through a 300-mesh sieve to prepare a sifted powder.

Subsequently, magnesium stearate was weighed at a mixing ratio shown in Table 3 and added to the sifted powder, followed by mixing for 5 minutes in a 13K bottle.

The mixture was molded at a compressive pressure of approximately 10 kN using a tableting machine (HandTab-200, Ichihashi Seiki Co., Ltd.) to obtain uncoated tablets (active ingredient (in terms of free form): 2.5%, round tablets, ⌀10.5 mm) each having a tablet mass of 400 mg.

(7 and 8) Preparation of Examples 8 and 9

Uncoated tablets supplemented with tocopherol and tocopherol acetic acid ester were produced according to the preparation procedures of Example 7.

(9) Preparation of Example 10

Compound (I), β-cyclodextrin, carmellose calcium, and sodium edetate were weighed at mixing ratios shown in Table 3 and mixed for 5 minutes in a 13K bottle.

The mixture was sifted through a 1000-μm mesh sieve and then sifted through a 300-mesh sieve to prepare a sifted powder.

Subsequently, magnesium stearate was weighed at a mixing ratio shown in Table 3 and added to the sifted powder, followed by mixing for 5 minutes in a 13K bottle.

The mixture was molded at a compressive pressure of approximately 10 kN using a tableting machine (HandTab-200, Ichihashi Seiki Co., Ltd.) to obtain uncoated tablets (active ingredient (in terms of free form): 2.5%, round tablets, ⌀10.5 mm) each having a tablet mass of 400 mg.

(10) Preparation of Comparative Example 2

Compound (I), D-mannitol, and carmellose calcium were weighed at mixing ratios shown in Table 4 and mixed for 5 minutes in a 13K bottle.

The mixture was sifted through a 1000-μm mesh sieve and then sifted through a 300-mesh sieve to prepare a sifted powder.

Subsequently, magnesium stearate was weighed at a mixing ratio shown in Table 4 and added to the sifted powder, followed by mixing for 5 minutes in a 13K bottle.

The mixture was molded at a compressive pressure of approximately 10 kN using a tableting machine (HandTab-200, Ichihashi Seiki Co., Ltd.) to obtain uncoated tablets (active ingredient (in terms of free form): 2.5%, round tablets, ⌀10.5 mm) each having a tablet mass of 400 mg.

(11) Preparation of Comparative Example 3

Ascorbic acid was pulverized at the number of revolutions of 1800 rpm using a beta mill (RM-201, manufactured by Medicatec Inc.). Compound (I), D-mannitol, carmellose calcium, and the ascorbic acid were weighed at mixing ratios shown in Table 4 and mixed for 5 minutes in a 13K bottle.

The mixture was sifted through a 1000-μm mesh sieve and then sifted through a 300-mesh sieve to prepare a sifted powder.

Subsequently, magnesium stearate was weighed at a mixing ratio shown in Table 4 and added to the sifted powder, followed by mixing for 5 minutes in a 13K bottle.

The mixture was molded at a compressive pressure of approximately 10 kN using a tableting machine (HandTab-200, Ichihashi Seiki Co., Ltd.) to obtain uncoated tablets (active ingredient (in terms of free form): 2.5%, round tablets, ⌀10.5 mm) each having a tablet mass of 400 mg.

(12 to 17) Preparation of Comparative Examples 4 to 9

Uncoated tablets supplemented with sodium bisulfite, sodium sulfite, erythorbic acid, cysteine hydrochloride, sodium pyrosulfite, and butylhydroxyanisole were produced according to the preparation procedures of Comparative Example 3.

The numerals in the tables described below represent contents (mg) in the tablets.

TABLE 3

| | Example 2 | Example 3 | Example 4 | Example 5 | Example 6 | Example 7 | Example 8 | Example 9 | Example 10 |
|---|---|---|---|---|---|---|---|---|---|
| Compound (I) | 17.56 | 17.56 | 17.56 | 17.56 | 17.56 | 17.56 | 17.56 | 17.56 | 17.56 |
| (mg in terms of free form) | 10 | 10 | 10 | 10 | 10 | 10 | 10 | 10 | 10 |
| Mannitol (Parteck M100, Merck) | 322.4 | 322.4 | 322.4 | 322.4 | 322.4 | 322.4 | 322.4 | 322.4 | — |
| Carmellose calcium (E.C.G-505, Gotoku Chemical Co., Ltd.) | 40 | 40 | 40 | 40 | 40 | 40 | 40 | 40 | 40 |
| Magnesium stearate (Taihei Chemical Industrial Co., Ltd., general product) | 8 | 8 | 8 | 8 | 8 | 8 | 8 | 8 | 8 |
| Sodium edetate (Dojin Laboratories, for testing and research) | 12 | — | — | — | — | — | — | — | — |
| Citric acid hydrate (Wako Pure Chemical Industries, Ltd., Japanese Pharmacopoeia) | — | 12 | — | — | — | — | — | — | — |
| Dibutylhydroxytoluene (Wako Pure Chemical Industries, Ltd., Wako special grade) | — | — | 12 | — | — | — | — | — | — |
| Propyl gallate (Wako Pure Chemical Industries, Ltd., Wako first grade) | — | — | — | 12 | — | — | — | — | — |
| Magnesium citrate (anhydrous) (Santa Cruz Biotechnology, for research) | — | — | — | — | 12 | — | — | — | — |
| Soybean lecithin (Nacalai Tesque, Inc., for chemistry) | — | — | — | — | — | 12 | — | — | — |
| Tocopherol (Tokyo Chemical Industry Co., Ltd., Tokyo Kasei first grade) | — | — | — | — | — | — | 12 | — | — |
| Tocopherol acetic acid ester (Junsei Chemical Co., Ltd., Junsei special grade) | — | — | — | — | — | — | — | 12 | — |
| β-Cyclodextrin (Nihon Shokuhin Kako Co., Ltd., B100H) | — | — | — | — | — | — | — | — | 334.4 |
| Tablet | 400 | 400 | 400 | 400 | 400 | 400 | 400 | 400 | 400 |

TABLE 4

|  | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| Compound (I) (mg in terms of free form) | 17.56 10 | 17.56 10 | 17.56 10 | 17.56 10 | 17.56 10 | 17.56 10 | 17.56 10 | 17.56 10 |
| Mannitol (Parteck M100, Merck) | 334.4 | 322.4 | 322.4 | 322.4 | 322.4 | 322.4 | 322.4 | 322.4 |
| Carmellose calcium (E.C.G-505, Gotoku Chemical Co., Ltd.) | 40 | 40 | 40 | 40 | 40 | 40 | 40 | 40 |
| Magnesium stearate (Taihei Chemical Industrial Co., Ltd., general product) | 8 | 8 | 8 | 8 | 8 | 8 | 8 | 8 |
| Ascorbic acid (Kishida Chemical Co., Ltd., special grade) | — | 12 | — | — | — | — | — | — |
| Sodium bisulfite (Wako Pure Chemical Industries, Ltd., special grade reagent) | — | — | 12 | — | — | — | — | — |
| Sodium sulfite (Wako Pure Chemical Industries, Ltd., special grade reagent) | — | — | — | 12 | — | — | — | — |
| Erythorbic acid (Junsei Chemical Co., Ltd., Junsei special grade) | — | — | — | — | 12 | — | — | — |
| Cysteine hydrochloride (Nacalai Tesque, Inc., special grade reagent) | — | — | — | — | — | 12 | — | — |
| Sodium pyrosulfite (Wako Pure Chemical Industries, Ltd., Japanese Pharmacopoeia) | — | — | — | — | — | — | 12 | — |
| Butylhydroxyanisole (Wako Pure Chemical Industries, Ltd., Wako special grade) | — | — | — | — | — | — | — | 12 |
| Tablet | 400 | 400 | 400 | 400 | 400 | 400 | 400 | 400 |

(3) Evaluation Method and Results

The tablets of Examples 2 to 10 and Comparative Examples 2 to 9 were left under conditions involving 40° C., 75% RH, and 1 week, 2 weeks, or 1 month. Then, the amount of related substances was measured by HPLC (1290 Infinity, Agilent Technologies, Inc.).

The results are shown in Tables 5 and 6. The amount of increase from the initial total amount of related substances was shown to be suppressed in Examples 2 to 10.

The numerals in the tables described below represent the total contents (%) of related substances.

TABLE 5

|  | Example 2 | Example 3 | Example 4 | Example 5 | Example 6 | Example 7 | Example 8 | Example 9 | Example 10 |
|---|---|---|---|---|---|---|---|---|---|
| Type of additive | Sodium edetate | Citric acid hydrate | Dibutyl-hydroxy-toluene | Propyl gallate | Magnesium citrate (anhydrous) | Soybean lecithin | Tocopherol | Tocopherol acetic acid ester | β-Cyclodextrin |
| 40° C./75% RH/1 week | 1.06 | 0.39 | 1.67 | 0.21 | 1.25 | 1.91 | 0.68 | 1.35 | 0.56 |
| 40° C./75% RH/2 weeks | 1.84 | 0.88 | 2.56 | 0.60 | 1.60 | 3.30 | 1.13 | 2.18 | 1.01 |
| 40° C./75% RH/1 month | 3.44 | 3.49 | 4.45 | 1.31 | 7.31 | 6.73 | 2.17 | 4.88 | 2.40 |

TABLE 6

|  | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| Type of additive |  | Ascorbic acid | Sodium bisulfite | Sodium sulfite | Erythorbic acid | Cysteine hydrochloride | Sodium pyrosulfite | Butyl-hydroxy-anisole |
| 40° C./75% RH/1 week | 3.50 | 34.75 | 6.61 | 12.43 | 19.79 | 3.47 | 6.50 | 2.79 |

TABLE 6-continued

| | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|
| 40° C./75% RH/2 weeks | 5.25 | 53.76 | 8.17 | 13.76 | 32.42 | 6.71 | 7.30 | 6.15 |
| 40° C./75% RH/1 month | 10.62 | 73.65 | 11.71 | 16.08 | 52.49 | 10.08 | 12.08 | 13.65 |

The invention claimed is:

1. A pharmaceutical preparation comprising [(1R,5S,6S)-6-(aminomethyl)-3-ethylbicyclo[3.2.0]hept-3-en-6-yl]acetic acid monobenzenesulfonate of formula (I):

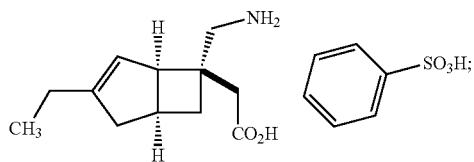

(i) one or two or more excipients;
(ii) one or two or more disintegrants; and
(iii) citric acid hydrate and tocopherol,
wherein the pharmaceutical preparation is a tablet, and each of the citric acid hydrate and the tocopherol is present at 0.01% to 10% by weight of the total weight of the uncoated tablet.

2. The pharmaceutical preparation of claim 1, wherein (i) is D-mannitol.

3. The pharmaceutical preparation of claim 2, wherein the D-mannitol has an average particle size of 100 μm or smaller.

4. The pharmaceutical preparation of claim 1, wherein each of the citric acid hydrate and the tocopherol is present at 0.1 to 3.0% by weight of the total weight of the uncoated tablet.

5. The pharmaceutical preparation of claim 1, further comprising magnesium stearate.

6. The pharmaceutical preparation of claim 5, wherein the magnesium stearate is present at 1 to 3% by weight of the total weight of the preparation.

7. A method of producing the pharmaceutical preparation of claim 5, comprising mixing [(1R,5S,6S)-6-(aminomethyl)-3-ethylbicyclo[3.2.0]hept-3-en-6-yl]acetic acid monobenzenesulfonate of formula (I):

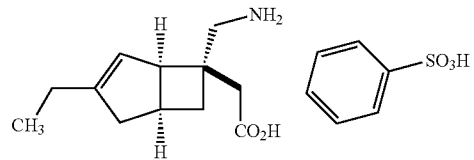

with
(i) one or two or more components selected from the group consisting of D-mannitol, lactose, corn starch, and crystalline cellulose;
(ii) carmellose calcium; and
subsequently adding magnesium stearate, followed by directly compressing the preparation to produce the tablet.

8. The pharmaceutical preparation of claim 1, wherein the compound of formula (I) is present at 0.5 to 5% by weight of the total weight of the preparation.

9. The pharmaceutical preparation of claim 1, wherein each of the citric acid hydrate and the tocopherol is present at 0.1 to 3.0% by weight of the total weight of the uncoated tablet.

10. A pharmaceutical preparation comprising [(1R,5S,6S)-6-(aminomethyl)-3-ethylbicyclo[3.2.0]hept-3-en-6-yl]acetic acid monobenzenesulfonate of formula (I):

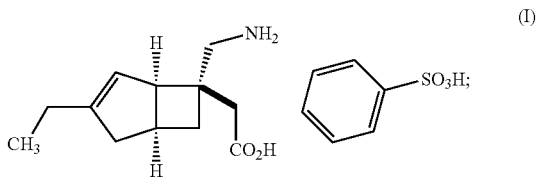

(i) one or two or more components selected from the group consisting of D-mannitol, lactose, corn starch, and crystalline cellulose;
(ii) carmellose calcium;
(iii) citric acid hydrate and tocopherol,
wherein the pharmaceutical preparation is a tablet, and each of citric acid hydrate and tocopherol is present at 0.01% to 10% by weight of the total weight of the uncoated tablet.

11. The pharmaceutical preparation of claim 10, wherein the carmellose calcium is present at 5 to 15% by weight of the total weight of the preparation.

12. The pharmaceutical preparation of claim 10, wherein the component (i) is D-mannitol.

13. The pharmaceutical preparation of claim 10, further comprising magnesium stearate.

14. The pharmaceutical preparation of claim 13, wherein the magnesium stearate is present at 1 to 3% by weight of the total weight of the preparation.

15. The pharmaceutical preparation of claim 10, wherein the compound of formula (I) is present at 0.5 to 5% by weight of the total weight of the preparation.

16. A method of stabilizing a pharmaceutical preparation comprising producing a pharmaceutical preparation comprising [(1R,5S,6S)-6-(aminomethyl)-3-ethylbicyclo[3.2.0]hept-3-en-6-yl]acetic acid monobenzenesulfonate of formula (I):

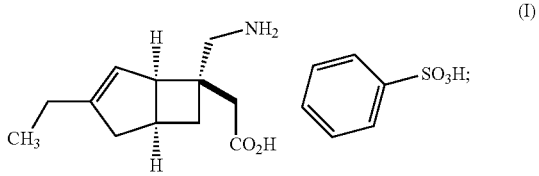

(i) one or two or more components selected from the group consisting of D-mannitol, lactose, corn starch, and crystalline cellulose;
(ii) carmellose calcium; and
(iii) citric acid hydrate and tocopherol,
wherein the citric acid hydrate and the tocopherol stabilize the pharmaceutical preparation.

* * * * *